United States Patent [19]

Ferrari et al.

[11] Patent Number: 5,284,832
[45] Date of Patent: Feb. 8, 1994

[54] IRON COMPLEXES CONTAINING CONALBUMIN AND ITS DERIVATIVES

[75] Inventors: Gianni Ferrari, Milan; Pier G. Pagella, Frazione Catraglia; Oscar Baiardo, Lainate, all of Italy

[73] Assignee: Mediolanum Farmaceutici S.p.A., Italy

[21] Appl. No.: 960,842

[22] Filed: Oct. 14, 1992

[30] Foreign Application Priority Data

Oct. 16, 1991 [IT] Italy .................. MI 91A002738

[51] Int. Cl.$^5$ .................. C07K 3/08; C07K 3/04; A61K 37/00
[52] U.S. Cl. .................. 514/21; 530/362; 530/367; 530/368; 530/400; 530/410
[58] Field of Search .............. 530/362, 367, 368, 400, 530/410; 514/21

[56] References Cited

U.S. PATENT DOCUMENTS

| | | | |
|---|---|---|---|
| 505,986 | 10/1893 | Marfori et al. | 530/367 |
| 523,688 | 7/1894 | Schmiedeberg | 530/362 |
| 929,452 | 7/1909 | Laves | 530/367 |
| 1,027,967 | 5/1912 | Zuckmayer | 530/367 |
| 3,959,249 | 5/1976 | Antonini | 530/368 |
| 4,493,829 | 1/1985 | Sportoletti et al. | 530/367 |
| 4,939,092 | 7/1990 | Villani et al. | 530/400 |
| 5,164,486 | 11/1992 | Tsunoo et al. | 530/362 |

FOREIGN PATENT DOCUMENTS

| | | |
|---|---|---|
| 2-001500 | 1/1990 | Japan . |
| 16152 | of 1908 | United Kingdom . |
| 9107426 | 5/1991 | World Int. Prop. O. . |

Primary Examiner—Michael G. Wityshyn
Assistant Examiner—C. Sayala
Attorney, Agent, or Firm—Oliff & Berridge

[57] ABSTRACT

Iron complexes with conalbumin and its derivatives, such as acetylconalbumin and succinylconalbumin, with an iron content ranging from 2 to 30% by weight, useful for the treatment of sideropenic and hypochromic anaemia, preparation process and pharmaceutical compositions containing them as active ingredients.

14 Claims, No Drawings

IRON COMPLEXES CONTAINING CONALBUMIN AND ITS DERIVATIVES

PRIOR ART

Iron—present in all body tissues—plays a basic physiological role. The body of a healthy adult contains 4-5 g of iron on an average. Single iron content values may vary from 3 to 6 g depending on body weight, total circulating haemoglobin and metal reserves.

Iron reserves, in the form of iron bound with apoferritin and haemosiderin, account for 20-30% of the total. 60-65% of iron is concentrated as red corpuscles. Iron transfer from the point of absorption to deposits is performed by transferring. Other non-hemic compounds containing iron are distributed in the various tissues.

The iron required by metabolism is yielded by absorption through the diet: iron is reduced in the stomach to ferrous ion, later absorbed by the cells of duodenum and jejunum, and then passes directly to the blood flow.

The factors influencing iron absorption are several: intraluminal factors (intestinal secretion and conditions of same), state of intestinal mucosa, and body factors (iron turnover, erythropoiesis). Iron loss due to menstruation and pregnancy, insufficient diet, malabsorption by children and old people due to alterations of the aforesaid factors bring about iron deficiencies which result frequently in serious clinical cases. Troubles affecting growth or baby feeding, tachycardia, shortness of breath, anginous type pains, vertigo are described as symptoms of iron deficiency.

Iron deficiency involves the entire organism and hypochromic anaemia constitutes the last stage of the disease. Epidemiologic research has evidenced that about 50% of sucklings exhibit iron deficiencies in the absence of anaemia vs. 25% sucklings affected by anaemia. 30% of children exhibit iron deficiency in the absence of anaemia, just like 90% of pregnant women who, unless duly treated, develop serious anaemia to an extent of 30%. (Fairbanks V. F. and Butler E.—Iron Deficiency: Hematology, Williams W. J.—New York 1977).

When sideropenic or anaemic patients undergo martial treatment, iron deficiency symptoms usually disappear and, if the therapeutical iron dose is adequate, there is a daily increase in average haemoglobin values. In most cases, however, it is not sufficient to carry on martial treatment to the attainment of normal haemoglobin values and therapy must be continued for several months, until anaemia is defeated. (Wurtrable M. M.—Clinical Hematology, Lea and Fibiger—Philadelphia 1967, 1974).

This means that martial treatments have to be prolonged and, in not very serious cases, involve the oral administration of iron salts, such as inorganic salts (ferrous sulphate, ferric chloride) or organic salts (citrate, fumarate, gluconate, etc.). At this point, there may be a problem of intolerance and toxicity, raised at the gastrointestinal level by a number of iron salts, mainly inorganic salts.

A considerable progress has been secured by the use of ferritin, a ferric globulin consisting of a protein—apoferritin—that surrounds trivalent iron.

Ferritin does not damage gastrointestinal walls, but, owing to the reduced availability of the source of extraction (equine and bovine spleen), it is very expensive. Recently, problems have been brought about by the use of bovine organs, potential transmitters of slow unconventional viruses (BSE).

Anyway, the results obtained by using ferritins demonstrate that the optimal iron carrier securing an oral martial treatment without side effects liable to damage the gastrointestinal apparatus is of a protein nature.

Thus, animal or vegetable proteins, either as are or modified (albumins, caseins, from soybean, etc.) have been used as iron carriers. The interaction between the said proteins and iron salts, however, gives non-homogeneous and scarcely soluble complexes with low iron content.

As is known, under physiological conditions, conalbumin can secure a bond with iron (a conalbumin molecule binds two iron atoms). Nevertheless, it is impossible to exploit this characteristic for treatment purposes because conalbumin has a molecular weight of 80,000 Da., hence it can only bind 0.14% iron.

SUMMARY

It has been surprisingly found that iron complexes containing conalbumin and its derivatives, such as acetylconalbumin and succinylconalbumin, can be obtained with an iron content ranging from 2 to 30% by weight. The said complexes have a high stability, a high solubility at physiological pH values, as well as high bioavailability and tolerability. Hence, they are fit for the preparation of pharmaceutical compositions to be used in the treatment of sideropenic and hypochromic anaemia.

The said iron complexes are prepared according to the following procedure:
a) a conalbumin aqueous solution from egg albumin is treated with acetic anhydride or succinic anhydride;
b) a conalbumin or acetylconalbumin or succinylconalbumin aqueous solution is allowed to react with an organic or inorganic iron compound aqueous solution.

DETAILED DESCRIPTION OF THE INVENTION

The properties of iron complexes containing conalbumin and its derivatives as well as the relevant preparation procedure according to the invention are as described hereinafter.

The invention is referred to a new class of iron complexes prepared by allowing conalbumin, acetylconalbumin and succinylconalbumin to react with organic and/or inorganic iron compounds. The said complexes contain a high percentage of bioavailable iron, exhibit a high tolerability and prove to be particularly efficacious for prophylaxis and for the treatment of sideropenic and hypochromic anaemia.

The material used for the preparation of such complexes is conalbumin obtained, by known ways, from egg albumin.

Conalbumin is dissolved in distilled water or saline solution containing low molarity sodium or potassium bicarbonate (0.1 to 0.5M) and the pH is brought to 9.5-10.5 by sodium hydroxide addition (N/10-N/2).

Then, acetic or succinic anhydride is added slowly along with an N/10 sodium hydroxide solution, so as to keep pH values from 7.5 to 8.5.

The solution is kept under stirring for some time, to desired pH stabilization, whereupon it is filtered and acidified with an acid solution (e.g. HCl 5N) to a pH equal to 3-3.5. The precipitate thus obtained is separated by filtration. The precipitate is suspended in distilled water and dissolved by addition of N sodium hydroxide, to a pH equal to 7.0–8.0.

The resulting solution is made limpid by filtration or centrifugation. Then, the precipitation, filtration, solubilization and clarification operations are repeated and, finally, the limpid solution is dialyzed or ultrafiltered and freeze-dried.

The product consists of acetylated or succinylated conalbumin, where the acetylation or succinylation level is a function of the quantity of acetic or succinic anhydride used. Such a level preferably ranges from 20% to 100%.

Acetyl- or succinylconalbumin, prepared as described above, is dissolved in distilled water and added slowly, under stirring, at ambient temperature, with an aqueous solution of an iron glucide derivative, either iron saccharate or iron fructate, with an acetyl-or succinylconalbumin/iron weight ratio ranging from 1:0.25 to 1:2. The concentration of acetyl- or succinylconalbumin solution preferably ranges from 2% to 25% by weight, while that of the iron glucide derivative solution preferably ranges from 2% to 20% by weight.

The mixture is kept under stirring for 1–3 hours, then it is treated slowly with HCl N/10 until pH lowers from 7.0 to 5.0, which brings about product precipitation.

The precipitate is recovered by filtration or centrifugation, washed with an HCl dilute solution, suspended in distilled water and redissolved by the slow addition of an N sodium hydroxide solution to pH 7.

The limpid solution is dialyzed or ultrafiltered and lyophylized. The product thus obtained—consisting of ferroacetyl- or ferrosuccinylconalbumin, has a complexed iron content ranging from 2% to 30% by weight and a proteic nitrogen content ranging from 10% to 15%.

As an alternative, the acetyl- or succinylconalbumin solution is allowed to react with an inorganic ferric salt solution, preferably $FeCl_3$ hexahydrate, with an acetyl- or succinylconalbumin/iron weight ratio ranging from 1:0.1 to 1:2, at ambient temperature, under stirring for 1–3 hours.

The concentration of the inorganic iron solution preferably ranges from 2% to 10% by weight and that of the acetyl- or succinylconalbumin solution preferably ranges from 2% to 25%.

The precipitate thus obtained is treated as described above. The final product resulting from lyophilization consists of ferroacetyl- or ferrosuccinylconalbumin and has a complexed iron content ranging from 1% to 10% by weight, the proteic nitrogen content ranging from 12% to 15.5%.

The described procedure is also followed to prepare the iron conalbumin complex. For this purpose, a conalbumin solution is allowed to react either with an iron glucide derivative solution, in a conalbumin/iron ratio ranging from 1:0.25 to 1:2, or with a ferric chloride solution, in a conalbumin/iron ratio ranging from 1:0.1 to 1:2, under stirring for 1–3 hours. The concentration of the conalbumin solution preferably ranges from 2% to 25%, that of the iron glucide derivative preferably ranges from 2% to 20%, and the one of iron salt preferably ranges from 2% to 10%.

In conalbumin treatment with iron glucide derivatives, an iron/conalbumin complex with a complexed iron content ranging from 2% to 25% by weight and a proteic nitrogen content ranging from 11% to 15% is obtained.

In conalbumin treatment with $FeCl_3$, an iron-conalbumin complex with a complexed iron content ranging from 1% to 8% by weight and a proteic nitrogen content ranging from 12.5% to 15.5% is obtained.

The complexes obtained with iron chloride exhibit an iron content that is significantly lower than in the complexes obtained by treatment with iron glucide derivatives; each product type, however, has a specific therapeutical use.

The iron contained in the complexes covered by the invention is fully bound: the absence of free iron is checked by precipitation with ammonium sulphate and HCl N/10 and demonstrated by total solubility in an alkaline environment, where iron ion precipitates. Iron is probably bound with the protein structure by means of a hydroxide bond: other iron atoms later bind with each other thus forming micelles surrounded and embodied by the protein chain.

The precipitation test with ammonium sulphate is conducted with addition of a 30% (vol./wt.) ammonium sulphate solution to a 10% solution of the test complex.

A precipitate identical to the starting complex is obtained: it is still soluble in water, while no free iron is contained in the supernatant solution.

The complexes covered by the invention are stable in an acid environment (they are not hydrolyzed by gastric enzymes) and are endowed with good solubility in an alkaline environment, a property that is indispensable to secure full bioavailability at the level of the intestinal apparatus, the body organ meant for iron absorption, with increased sideraemia levels at no detriment of the intestinal mucosa.

When administered to test animals by the oral way, they can raise sideraemia levels without side-effects on the gastrointestinal mucosa. Moreover, the absorption of the iron contained in the complexes covered by the invention takes place by the normal absorption ways, through natural mechanisms controlling iron absorption by the intestine.

The invention is, therefore, referred also to the pharmaceutical formulations (ampoules, tablets, capsules, syrups, granules in sachets, etc.) containing effective quantities of iron complexes with conalbumin, acetyl- or succinylconalbumin useful in treatment and prophylaxis of sideropenic anaemia and hypochrosis.

EXAMPLE 1 a) Preparation of Acetyl- or Succinylconalbumin 10 g conalbumin from egg albumin are dissolved in 100 ml $H_2O$ and added slowly, under stirring, with NaOH 1N to pH 10. Then, 5 ml acetic anhydride or 5 g succinic anhydride are added slowly along with NaOH N/10 to keep the solution pH at approx. 8.0. At the end of the above additions, the solution is kept under stirring for 60 minutes, at ambient temperature.

The opalescent solution is filtered and centrifuged until clear, then it is acidified slowly with HCl to pH 3-3.5.

The precipitate thus formed is filtered; then, it is suspended in 100 ml $H_2O$ and added with NaOH to complete dissolution (pH=approx. 8). The solution is filtered once more and acidified slowly with HCl to pH 3-3.5.

The precipitate is filtered, suspended in 100 ml $H_2O$ and redissolved by addition of NaOH to pH 8.

The clear solution is dialyzed or ultrafiltered and then lyophilized.

The lyophilized product thus obtained consists of 7 g acetylated or succinylated conalbumin, the acetylation or succinylation of which is equal to 95%.

The acetylation degree is expressed as percentage of acetylated groups vs. the groups able to be acetylated of the starting conalbumin and is determined by the ninhydrin reaction of the free amine groups (J. Biol. Chem., 211, 1954, 907).

The succinylation degree is expressed as percentage of succinylated groups vs. the free amine groups of the starting conalbumin and is determined by the ninhydrin reaction of the free amine groups (J. Biol. Chem., 211, 1954, 907).

b) Preparation of the Ferroacetyl or Ferrosuccinyl Conalbumin Complex by the Use of Iron Saccharate 3 g acetylated or succinylated conalbumin, obtained as described under a), are dissolved in 60 ml $H_2O$ (pH 7.5) and added slowly, under stirring, with a solution of 6 g iron saccharate (iron content=20%) in 15 ml $H_2O$. At the end of this addition, the solution is kept under stirring for 120 minutes, at ambient temperature (pH 7). The solution thus obtained is acidified slowly with HCl 0.1N to precipitation (pH 5).

The precipitate is filtered, washed with 30 ml HCl 0.01N, suspended in 30 ml $H_2O$, and redissolved by slow addition of NaOH 1N to pH 7. The clear solution is then dialyzed or ultrafiltered and lyophilized.

The lyophilized solid product (2.7 g) has a complexed iron content equal to 19.1% and a proteic nitrogen content of 13%.

EXAMPLE 2

Preparation of the Ferroacetyl or Ferrosuccinyl Conalbumin Complex by the Use of Iron Fructate An iron complex starting from 3 g acetylated or succinylated conalbumin and 6 g iron fructate (iron=10%) is obtained via the same procedure as described in Example 1.

The lyophilized solid product has a complexed iron content equal to 12.4% and a proteic nitrogen content of 12.5%.

EXAMPLE 3

Preparation of the Ferroacetyl or Ferrosuccinyl Conalbumin Complex by the Use of Ferric Chloride 1 g acetylated or succinylated conalbumin obtained as described in Example 1 is dissolved in 10 ml water (pH 7) and added with 0.83 g ferric chloride hexahydrate dissolved in 10 ml $H_2O$ (pH 2). The solution is kept under stirring for 60 minutes. The precipitate is filtered, washed with 30 ml HCl 0.01N and redissolved by slow addition of NaOH 1N to pH 7.5.

The solution is filtered, dialyzed or ultrafiltered, and lyophilized.

The lyophilized solid product has a complexed iron content equal to 4.5% and a proteic nitrogen content of 14.2%.

EXAMPLE 4

Preparation of the Iron-Conalbumin Complex by the Use of Iron Fructate 5 g conalbumin are dissolved in 200 ml $H_2O$ (pH 3.5) and added with a solution of 10 g iron fructate (iron=10%) in 100 ml $H_2O$.

The solution is kept under stirring for 60 minutes.

The precipitate is separated by centrifugation, washed with distilled water and dissolved thoroughly with NaOH to pH 7.5.

The solution is filtered, dialyzed or ultrafiltered, and lyophilized.

The lyophilized solid product has a complexed iron content equal to 12.5% and a proteic nitrogen content of 12.5%.

EXAMPLE 5

Preparation of the Iron-Conalbumin Complex by the Use of Iron Saccharate

An iron complex starting from 5 g conalbumin and 5 g iron saccharate (iron=20%) is obtained via the same procedure as described in Example 4.

The lyophilized solid product has a complexed iron content equal to 17.5% and a protein nitrogen content of 11.9%.

EXAMPLE 6

Preparation of the Iron-Conalbumin Complex by the Use of Ferric Chloride

An iron complex starting from 1 g conalbumin and 0.83 g ferric chloride is obtained via the same procedure as described in Example 4.

The freeze-dried solid product has a complexed iron content equal to 5% and a protein nitrogen content of 15.1%.

EXAMPLE 7

Preparation of Pharmaceutical Compositions containing Iron Complexes with Conalbumin and its Derivatives Ampoules containing 20 to 200 mg iron in the form of conalbumin or acetyl- or succinylconalbumin complexes and, in addition, aqueous solvent, flavouring agents, stabilizers, etc., as usually used in pharmaceuticals.

Tablets containing 20 to 200 mg iron in the form of conalbumin or acetyl- or succinylconalbumin complexes and, in addition, excipients, disintegrants, etc., as usually used in pharmaceuticals.

Capsules containing 20 to 200 mg iron in the form of conalbumin or acetyl- or succinylconalbumin complexes.

Single-dose sachets for granules containing 10-20-40-100 mg iron in the form of conalbumin or acetyl- or succinylconalbumin complexes.

Syrups containing 1 to 20 mg/ml iron in the form of conalbumin or acetyl- or succinylconalbumin complexes and, in addition, aqueous solvent, flavouring agents, stabilizers, etc., as usually used in pharmaceuticals.

TOXICITY TESTS

Acute toxicity was assessed in mice. Iron complexes were administered by the oral way and in all cases LD50 proved to be higher than 4000 mg/kg.

When administered to mice by the oral way, the ferrous sulphate LD50 proved to be 1500 mg/kg.

Sideraemia after Oral Administration

The capacity of some iron complexes covered by the invention to raise sideraemia basal values was assessed in S. D. rats weighing 180–200 g, after 18 hours fast.

The products were administered by stomach probe two hours before rat sacrifice, at doses containing an equal amount of iron, i.e. 2 mg/kg.

Iron determination in serum was made by spectrophotometry with bathophenanthroline (colorimetric method, Boehringer Mannheim). Results are conveyed in Table 1.

TABLE 1

| Treatment | Serous iron µg/100 ml |
|---|---|
| Physiological saline | 145 ± 19.4 |
| Product of Example 1 | 331 ± 9.8 |
| Product of Example 4 | 315 ± 18.5 |
| Product of Example 5 | 296 ± 20.3 |
| Ferrous sulphate | 275 ± 39.8 |

We claim:

1. Iron complexes comprising iron and at least one of conalbumin and acetylconalbumin, with iron content ranging from 2 to 30% by weight.

2. Process for the preparation of iron complexes comprising iron and at least one of conalbumin and acetylconalbumin, with iron content ranging from 2 to 30% by weight, wherein
at least one of a conalbumin and acetylconalbumin aqueous solution is reacted with an aqueous solution of an organic iron compound consisting of an iron glucide derivative or an inorganic iron compound consisting of ferric chloride.

3. Process according to claim 2 wherein the iron glucide derivative is selected from the group consisting of iron saccharate and iron fructate.

4. Process according to claim 2, wherein the acetylconalbumin reaction with an organic iron compound is brought about by the slow addition, at ambient temperature, of a solution of said iron glucide derivative at a concentration ranging from 2 to 20% by weight to a solution of said acetylconalbumin at a concentration ranging from 2 to 25% by weight, under stirring for 1 to 3 hours and precipitating ferroacetylconalbumin by treatment with HCl which lowers the pH from 7 to 5.

5. Process according to claim 4 wherein the weight ratio of acetylconalbumin to the iron used in the preparation of ferroacetylconalbumin ranges from 1:0.25 to 1:2.

6. Process according to claim 2 wherein the precipitated ferroacetylconalbumin is separated from the solution, washed with an HCl dilute solution, redissolved in an NaOH solution and the solution thus obtained is dyalized or ultrafiltered and lyophilized.

7. Process according to claim 2 wherein the acetylconalbumin reaction with an inorganic iron compound is brought about by the addition, at ambient temperature, of a solution of ferric chloride at a concentration ranging from 2 to 10% by weight to an acetylconalbumin solution at a concentration ranging from 2 to 25% by weight, under stirring for 1 to 3 hours.

8. Process according to claim 2 wherein the acetylconalbumin to inorganic iron ratio ranges from 1:0.1 to 1:2.

9. Process according to claim 2 wherein the conalbumin reaction with an organic iron compound is brought about by the addition, at ambient temperature, of a solution of said iron glucide derivative at a concentration ranging from 2 to 20% by weight to a conalbumin solution at a concentration ranging from 2% to 25% by weight, under stirring for 1 to 3 hours.

10. Process according to claim 2 wherein conalbumin to inorganic iron ratio ranges from 1:0.25 to 1:2.

11. Process according to claim 2 wherein the conalbumin reaction with an inorganic iron compound is brought about by the addition, at ambient temperature, of a ferric salt solution at a concentration ranging from 2 to 10% by weight to a conalbumin solution at a concentration ranging from 2 to 25% by weight, under stirring for 1 to 3 hours.

12. Process according to claim 11 wherein the conalbumin to iron ratio ranges from 1:01 to 1:2.

13. Pharmaceutical compositions useful for the treatment of sideropenic and hypochromic anaemia, whose active ingredient is an iron complex comprising iron and at least one of conalbumin and acetylconalbumin, with an iron content ranging from 2 to 30% by weight.

14. Therapeutic method for the treatment of sideropenic and hypochromic anaemia consisting in administering an effective amount of iron complexes comprising iron and at least one of conalbumin and acetylconalbumin.

* * * * *